(12) United States Patent
Alemán Vázquez et al.

(10) Patent No.: US 9,862,658 B2
(45) Date of Patent: Jan. 9, 2018

(54) USE OF POLYMERS AS HETEROGENEOUS HYDROGEN DONORS FOR HYDROGENATION REACTIONS

(71) Applicant: INSTITUTO MEXICANO DEL PETRÓLEO, Mexico City (MX)

(72) Inventors: Laura Olivia Alemán Vázquez, Mexico City (MX); José Luis Cano Domínguez, Mexico City (MX); José Luis Garciá Gutiérrez, Mexico City (MX)

(73) Assignee: Instituto Mexicano del Petroleo, Mexico City (MX)

( * ) Notice: Subject to any disclaimer, the term of this patent is extended or adjusted under 35 U.S.C. 154(b) by 61 days.

(21) Appl. No.: 14/934,590

(22) Filed: Nov. 6, 2015

(65) Prior Publication Data
US 2016/0200644 A1    Jul. 14, 2016

(30) Foreign Application Priority Data
Nov. 6, 2014  (MX) .................. MX/A/2014/013477

(51) Int. Cl.
*C07C 5/10* (2006.01)
*C08G 63/197* (2006.01)
*C07C 5/03* (2006.01)

(52) U.S. Cl.
CPC .............. *C07C 5/10* (2013.01); *C07C 5/03* (2013.01); *C08G 63/197* (2013.01); *C07C 2101/14* (2013.01); *C07C 2101/16* (2013.01); *C07C 2521/04* (2013.01); *C07C 2523/42* (2013.01); *C07C 2531/06* (2013.01); *C07C 2601/14* (2017.05); *C07C 2601/16* (2017.05)

(58) Field of Classification Search
CPC .................................................. C07C 2531/06
See application file for complete search history.

(56) References Cited

U.S. PATENT DOCUMENTS

| | | |
|---|---|---|
| 3,413,212 A | 11/1968 | Weisz |
| 4,049,536 A | 9/1977 | Plumlee et al. |
| 4,077,867 A | 3/1978 | Aldridge et al. |
| 4,210,518 A | 7/1980 | Wilson et al. |
| 4,298,450 A | 11/1981 | Ross |
| 4,345,989 A | 8/1982 | Vernon et al. |
| 4,395,324 A | 7/1983 | Derbyshire et al. |
| 4,485,004 A | 11/1984 | Fisher et al. |
| 4,642,175 A | 2/1987 | Rudnick et al. |
| 4,696,733 A | 9/1987 | Tsao |
| 5,399,632 A | 3/1995 | Costello et al. |
| 7,576,240 B2 | 8/2009 | Murphy |
| 7,594,990 B2 | 9/2009 | Satchell, Jr. |
| 2011/0172461 A1 | 7/2011 | Rogers |

*Primary Examiner* — Sharon Pregler
*Assistant Examiner* — Alyssa L Cepluch
(74) *Attorney, Agent, or Firm* — Jason P. Mueller; Adams & Reese, LLP (57) ABSTRACT

The present disclosure covers the use of polymers or copolymers having a naphthalene-type unit in their structure as heterogeneous hydrogen transfer agents for hydrogenation, hydrotreatment or reduction reactions. These heterogeneous hydrogen transfer agents may or may not be supported on metallic oxides and may be used in the presence of reducing agents such as hydrogen or methane. These hydrogen donors, being solid at the reaction temperature, may be recovered from the reaction mixture and reused, and are thermally and chemically stable at temperatures up to above 450° C.

8 Claims, 5 Drawing Sheets

Polymer 1

R, R' = -OAr-, -COOAr-, -CH₂-CH₂-

USE OF POLYMERS AS HETEROGENEOUS HYDROGEN DONORS FOR HYDROGENATION REACTIONS

CROSS-REFERENCE TO RELATED APPLICATIONS

This application claims benefit of Mexican Application MX/A/2014/013477, which was filed Nov. 6, 2014, and is incorporated herein in its entirety by reference thereto.

TECHNICAL FIELD

The present disclosure relates to heterogeneous hydrogen donors, also known as heterogeneous hydrogen transfer agents. These hydrogen donors are constituted by polymers or copolymers that have in their structure one or more units of naphthalene, decalin, tetralin or more complex structural units that include one of these three compounds; they may be supported or extruded in metallic oxides such as alumina, silica, titania or caolin. Application of the compounds and methods disclosed herein covers any chemical reaction involving a reduction and operate in the presence of reducing agents such as hydrogen, methane and their mixtures. These hydrogen donors, being solids, may be easily recovered from the reacting mixture for reutilization, and their thermal stability allows for their use in reactions at temperatures up to 450° C.

BACKGROUND

Hydrogenation reactions are often hampered by a limited availability of hydrogen that must be transferred to the liquid phase before the reaction can start, and by the use of a low hydrogen partial pressure. Hydrogenation reactions may be favored by the use of hydrogen donors, compounds such as naphthalene that are reversibly hydrogenated-dehydrogenated in the reacting mixture. In this way, when using hydrogen donors in a particular hydrogenation reaction, the hydrogenation-dehydrogenation equilibrium of the hydrogen donor generates an additional amount of hydrogen atoms in the reaction environment, thus favoring the desired hydrogenation reaction.

A typical hydrogen donor is decalin (decahydronaphthalene), which in a hydrogenation reaction is in equilibrium with tetralin (1,2,3,4-tetrahydronaphthalene) and naphthalene. It must be pointed out that in the case of naphthalene, tetralin and decalin, their separation and recovery from the reaction mixture is usually difficult due to their high solubilities in the reactants, products and solvents.

dronaphthalene, following a mechanism of hydrogen transfer in the presence of the catalytic material.

U.S. Pat. No. 4,642,175 discloses the reduction of coke formation of heavy hydrocarbons by treatment with transition metals naphtenates at temperatures below 350° C. The product is stable and can be fed to subsequent processes such as catalytic and thermal cracking, including visbreaking and coking, with an improvement in liquid yields and lower coke formation.

U.S. Pat. No. 4,049,536 discloses a process for coal liquefaction to produce liquid hydrocarbons by means of the following stages: a) the coal is mixed with a non-hydrogen donor solvent and an orto-quinone compound to form a coal-in-liquid suspension, and b) the suspension is mixed with molecular hydrogen at a pressure and temperature adequate for coal hydroconversion and liquefaction. Ortoquinone acts as a hydrogenation catalyst, promoting coal hydrogenation in the liquefaction zone in the presence of molecular hydrogen without a hydrogen donor solvent.

U.S. Patent No. 20110172461 discloses a methodology for the recycling of a polymeric material that comprises a depolymerization of the material by heating in the presence of a hydrogen donor and a strong base. This method was developed for the recycling of polyethylene terephthalate via depolymerization by heating in the presence of a hydrogen donor and a strong base.

U.S. Pat. No. 4,395,324 discloses the use of a low-boiling-point hydrogen donor such as tetralin in a cracking process.

U.S. Pat. No. 4,696,733 discloses a process for the partial hydrogenation of polynuclear aromatic compounds using a manganese catalyst in the presence of hydrogen at high temperature. The resulting partially hydrogenated products are used as hydrogen donors in the thermal cracking process.

U.S. Pat. No. 5,399,632 discloses the hydrogenation of unsaturated copolymers, without the addition of hydrogen, using a hydrogen donor in the presence of a Group VII metal catalyst, more specifically a supported palladium catalyst.

U.S. Pat. No. 4,210,518 discloses improvement in liquid product yield obtained during coal or coke liquefaction using a hydrogen donor.

U.S. Pat. No. 4,345,989 discloses the conversion of coal to low-molecular-weight liquid hydrocarbons using a hydrogen donor solvent in the presence of an alkaline metal catalyst prepared by heating at a temperature above 800° F. in a reaction zone external to the liquefaction zone.

U.S. Pat. No. 4,485,004 discloses a process for the conversion of heavy hydrocarbons to lighter products by hydrocracking in the presence of a hydrogen donor having Naphthalene          Tetralin          Decalin U.S. Pat. No. 3,413,212 discloses a process for upgrading the properties of hydrocarbon cuts having boiling points above 204° C. using a crystalline aluminosilicate catalyst and a hydrogen donor at temperatures in the 290-593° C. range with the aim of obtaining hydrocarbon fractions in the gasoline range. The hydrogen donor is prepared by partial hydrogenation of polynuclear aromatic compounds, and is preferably 1,2,3,4-tetrahydronaphthalene and decahya boiling point above 200° C. and a hydrogenation catalyst made of cobalt, molybdenum, nickel, tungsten or a mixture of these.

U.S. Pat. No. 7,576,240 discloses the selective hydrogenation of double or triple bonds in organic molecules using a hydrogen donor.

U.S. Pat. No. 7,594,990 discloses a process where a hydrogen donor solvent is used to increase the residuals conversion in the ebullated bed residuals hydrocracking process. The hydrogen donor solvent is produced by means of hydroreforming reactions in the residuals hydrocracking. In this process the hydrogen donor solvent reduces the coke formation at the high operating temperatures.

U.S. Pat. No. 4,298,450 discloses a method for coal hydroconversion by treatment with a solvent at high temperatures and pressures, where an alcohol that contains a a-hydrogen atom, more specifically a secondary alcohol such as isopropanol is used as a hydrogen donor solvent.

U.S. Pat. No. 4,077,867 discloses a process for the catalytic hydroconversion of coal using a metallic compound and a hydrogen donor solvent in the presence of hydrogen. The preferred metallic compounds are made of molybdenum.

As disclosed in the aforementioned patents, liquid hydrogen donors such as tetralin or decalin may be well known; however, these compounds are expensive and their recovery and reuse is difficult; for these reasons, in certain embodiments of the present disclosure, we present heterogeneous hydrogen transfer agents, solids at reaction temperatures, which are constituted by polymers prepared from monomers that have a naphthalene type unit in order to participate in reduction reactions. The hydrogen transfer agents, as disclosed in various embodiments of the present disclosure, have fusion or decomposition temperatures above the required reaction temperature, in the range of 100 to 450° C., are chemically stable at the reaction conditions and have textural properties suitable for industrial application.

| Sample | BET surface area (m²/g) | Total pore volume (cm³/g) | Average pore diameter (Å) |
|---|---|---|---|
| Polymer 1 | 1.5688 | 0.004818 | 122.8340 |
| Polymer 1 extruded in silica | 135.2312 | 0.220202 | 48.6196 |

DESCRIPTION OF EMBODIMENTS

Reduction reactions are limited by the availability of hydrogen, that must be transferred to the liquid phase before the hydrogenation reaction can start, and by the hydrogen partial pressure; hydrogen donor polymers or copolymers presented in this disclosure provide an additional amount of hydrogen atoms for the hydrogenation reaction, since the naphthalene units present a hydrogenation-dehydrogenation equilibrium.

It is therefore an advantage of the present disclosure to apply these polymers and copolymers as hydrogen transfer agents to carry out hydrogenation reactions and in general any chemical reaction involving a reduction.

Another advantage of this disclosure is that the application of these heterogeneous hydrogen transfer agents in hydrogenation reactions and chemical reduction reactions is carried out in the presence of reducing agents such as hydrogen. This disclosure is an alternative for executing any reaction that involves the reduction of double bonds using heterogeneous hydrogen donors based upon naphthalene-type compounds that can be reversibly hydrogenated-dehydrogenated in the reaction mixture.

This disclosure is an alternative for executing any reaction that involves the reduction of double bonds using heterogeneous hydrogen donors based upon naphthalene-type compounds that can be reversibly hydrogenated-dehydrogenated in the reaction mixture.

Figure 1:
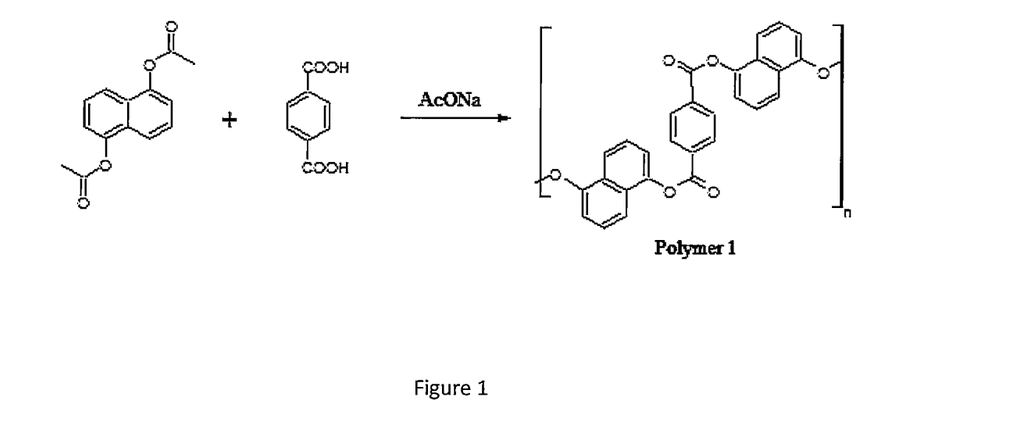
FIG. 1 shows the chemical structure of the hydrogen donor polymer, Polymer 1 (Poly-(1,4-bis(1,5-naphthalene-dioxy)benzenedicarboxylate)), according to an example embodiment of the present disclosure.
Figure 2:
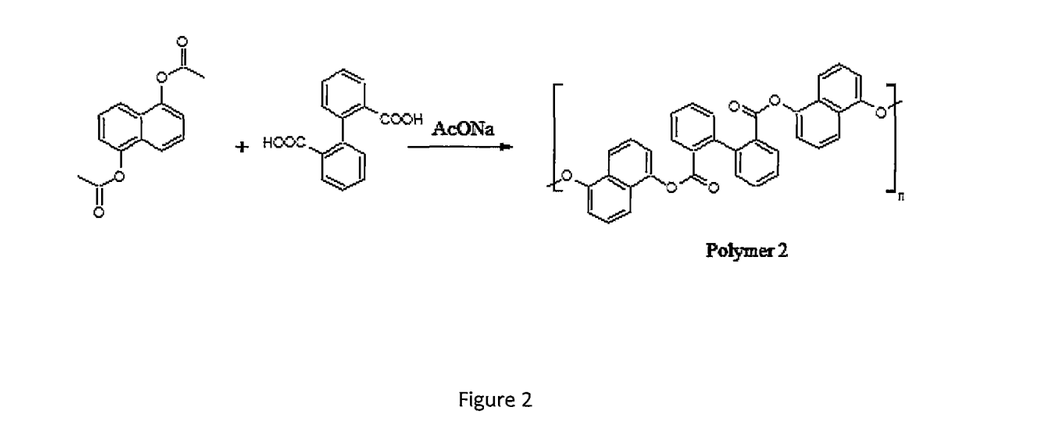
FIG. 2 shows the chemical structure of the hydrogen donor polymer, Polymer 2 (Poly-(2,2'-bis(1,5-naphthalene-dioxy)diphenyldicarboxylate)), according to an example embodiment of the present disclosure.

The present disclosure refers to the use of polymers or copolymers based upon the naphthalene unit, as particularly exemplified by polyester-type polymers with naphthalene units such as Polymer 1 and Polymer 2 shown in FIGS. 1 and 2, in hydrogenation reactions. These polymers present activity as hydrogen donors for reactions of reduction of double bonds between two carbon atoms in model molecules, either in batch or flow reactors, in which the properties of the heterogeneous hydrogen donor polymers include a fusion or decomposition temperature up to above 450° C., the possibility of being supported or extruded and of improving their textural properties such as surface area by admixing with clay-type materials or metallic oxides such as alumina, silica, titania or kaolin. Furthermore, the present disclosure describes the use of the aforementioned polymers and copolymers as heterogeneous hydrogen donors in any chemical reaction involving the reduction of chemical functional groups in the presence of a reducing agent such as hydrogen, methane or a mixture of the same.

Another advantage of the present disclosure is that these heterogeneous hydrogen donors may be used in chemical hydrogenation reactions by themselves or in combination with a catalyst.

A characteristic of this disclosure is that the synthesis of the polyester-type heterogeneous hydrogen donors derived from 1,5-dihydroxynaphthalene and from different carboxylic acids was based upon the works of Asrar, J.; Toriumi, H.; Watanabe, J.; Krigbaum, W. R.; Ciferri, A. J. Polym. Sci. Polym. Physics Ed., 21, 1119-1131, 1983; Acierno, D.; La Manita, F. P.; Polizzotti, G.; Ciferri, A.; Krigbaum, W. R.; Kotek, R. J. Polym. Sci. Polym. Physics Ed., 21, 2027-2036, 1983; Cai R.; Samulski, E. T. Macromolecules, 27, 135-140, 1994 and more recently Somogyi, A.; Bojkova, N.; Padias, A. B.; Hall, H. K. Jr.; Macromolecules, 38, 4067-4071, 2005. These references describe different techniques for the synthesis and give some physical properties of the resulting polymers.

Another characteristic of this disclosure is that the synthesis of the polyesters is carried out in two stages: the first stage is the acetylation of 1,5-dihydroxynaphthalene and the second stage is the polymerization of 1,5-diacetoxynaphthalene with dicarboxylic acids such as terephthalic, diphenic, 4,4'diphenyldicarboxylic or 1,4-naphthalenedicarboxylic acid, to obtain polymers such as the ones shown below.

Polymer 1

Polymer 2

Figure 3:
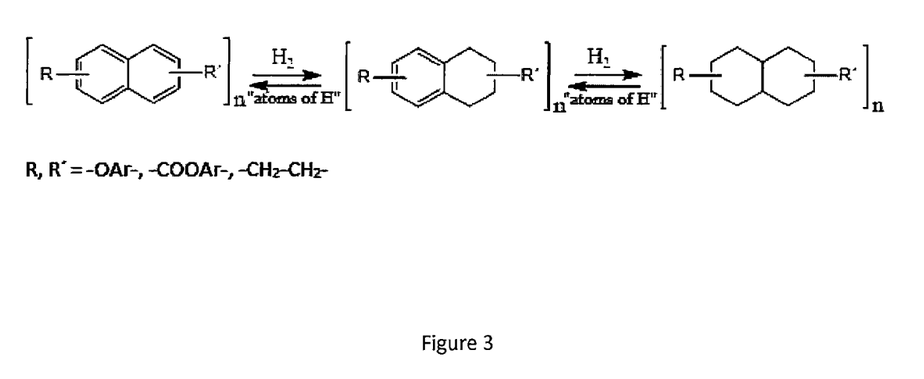
FIG. 3 shows hydrogenation-dehydrogenation of heterogeneous hydrogen donors having a naphthalene unit, according to an example embodiment of the present disclosure.
Figure 4:
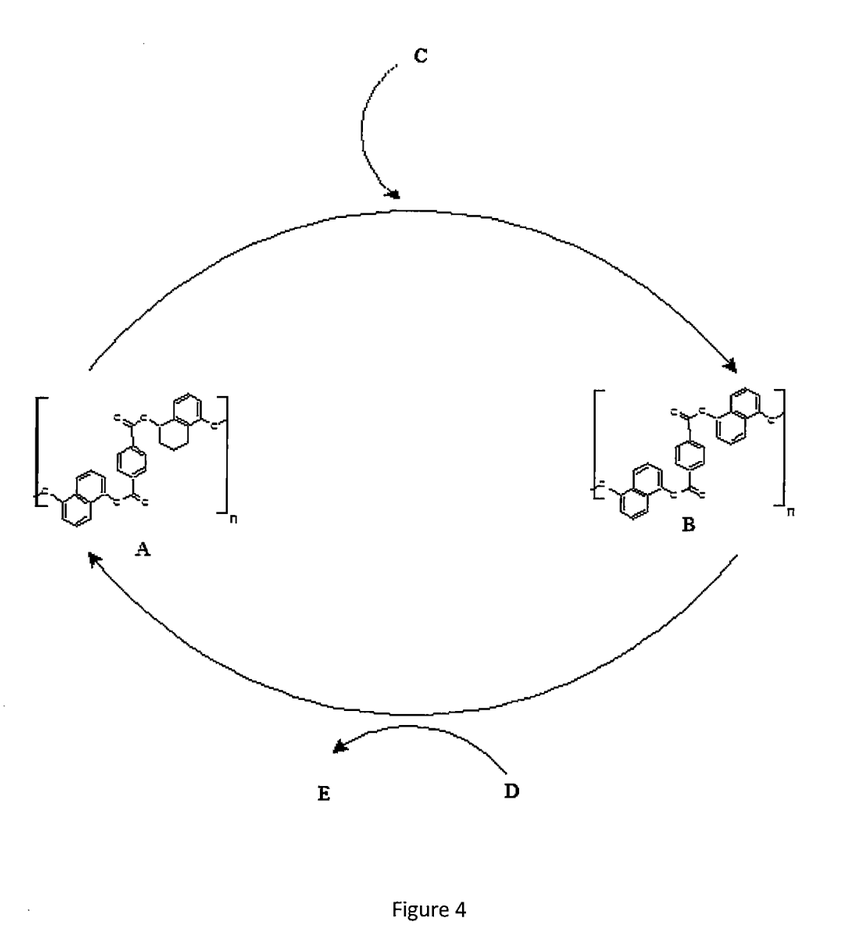
FIG. 4 shows a reaction scheme showing the hydrogenation-dehydrogenation process of the heterogeneous hydrogen donors object of the disclosure in the reduction of cyclohexene, according to an example embodiment of the present disclosure, where A is non-hydrogenated Polymer 1; B is hydrogenated Polymer 1; C is molecular hydrogen or methane; D is cyclohexene; and E is cyclohexane.

Besides, the present disclosure has the characteristic that heterogeneous hydrogen donors containing a naphthalene unit, when subjected to a reducing atmosphere such as hydrogen, methane, mixtures of hydrogen-methane or mixtures of gaseous hydrocarbons such as natural gas, undergo a reduction of the naphthalene ring to a partially hydrogenated ring with the structure of tetralin at appropriate temperatures and pressures.

Additionally, another characteristic of the present disclosure is that, since heterogeneous hydrogen donors are solids, they are easily recovered for posterior use, unlike conventional hydrogen donors such as tetralin or decalin.

Example 1

This example shows the synthesis of the heterogeneous hydrogen donor Polymer 1 (Poly-(1,4-bis(1,5-naphthalenedioxy)benzenedicarboxylate)). For example, 158.8 grams of 1,5-di acetoxynaphthalene, 108 grams of terephthalic acid and 0.533 grams of sodium acetate, previously mixed, were placed in a 1-liter stainless steel autoclave-type reactor, with mechanical agitator and temperature control. The reactor was closed and purged with nitrogen, heated to 275° C. and maintained for 2 hours at this temperature; during the reaction the acetic acid generated was eliminated by purging with nitrogen. After this 2-hour period, the temperature was raised to 300° C. for 1 hour, and then raised again to 350° C. for 2 hours. After this process, the reactor was cooled to ambient temperature, stopping agitation but maintaining the nitrogen atmosphere. The resulting polymer was washed with acetone, chloroform, toluene and again acetone and finally was dried at 100° C. for 1 hour in a vacuum stove.

Polymer 1

Example 2

This example shows the synthesis of the heterogeneous hydrogen donor Polymer 2 (Poly-(2,2'-bis(1,5-naphthalenedioxy)diphenyldicarboxylate)). For example, 2.4 grams of 1,5-diacetoxynaphthalene, 2.4 grams of 1,1'-diphenyl-2,2'-dicarboxylic acid and 0.01 grams of sodium acetate, previously mixed, were placed in a 1-liter stainless steel autoclave-type reactor, with mechanical agitator and temperature control. The reactor was closed and purged with nitrogen, heated to 280° C. and maintained for 1 hour at this temperature; during the reaction the acetic acid generated was eliminated by purging with nitrogen. After this 1-hour period, the temperature was raised to 340° C. ford hour, and then raised again to 360° C. for 2 hours. After this process, the reactor was cooled to ambient temperature, stopping agitation but maintaining the nitrogen atmosphere. The resulting polymer was washed with acetone, chloroform, toluene and again acetone and finally was dried at 100° C. for 1 hour in a vacuum stove.

Polymer 2

Example 3

This example shows the procedure to extrude Polymer 1 with silica-kaolin. For example, 33.9 grams of kaolin and 20.7 milliliters of water were mixed with 14.5 grams of Polymer 1, previously ground to a particle size under 100 micrometers, 20.8 grams of colloidal silica and 0.1 milliliters of formic acid to form an homogeneous paste; this paste was extruded in the shape of 2-mm diameter by 5-mm length cylinders and dried at 100° C. overnight in air atmosphere. Finally, the cylinders were calcined in a nitrogen atmosphere at 500° C. for 2 hours.

Example 4

This example shows the hydrogenation of Polymer 1 at a pressure between 30 and 80 atm. Hydrogenation was carried out in a stainless steel autoclave-type reactor. 20 grams of Polymer 1 were placed in the reactor under a nitrogen flow of 12 slph for purging, the temperature was raised first to 120 and then to 450° C., maintaining each temperature for 2 hours; finally the temperature was lowered to 430° C. and the nitrogen gas feed was changed to hydrogen, pressurizing the reactor and maintaining the desired temperature and pressure for 18 hours.

The results of the hydrogenation were assessed using solid-state C-13 nuclear magnetic resonance. In general, three chemical processes con be observed: the reduction of the carboxyl group to the corresponding ether, the hydrogenolysis of the ether group, and the hydrogenation of an aromatic ring of naphthalene generating the tetralin structure. A more detailed description of the spectroscopic evidence of these chemical processes follows.

Polymer 1 before hydrogenation showed 5 signals: 1) at 167 ppm, corresponding to the carboxyl (C=O) group; 2) at 147 ppm, corresponding to the carbon atom in the naphthyl group attached to the benzoate group (C—O—C(O)—C); 3) at 138 ppm, attributed to the carbon atom in the phenyl group attached to the carboxyl group (C—C(O)—O); 4) at 128 ppm, generated by the four aromatic carbons (C—H) of the phenyl group and the two aromatic carbons of the naphthyl group in the meta position to the carbon atom attached to the benzoate group (Cmeta-H and >Cmeta=); and 5) at 119 ppm, corresponding to one or both aromatic carbons of the naphthyl group in the ortho and para positions to the carbon atom attached to the benzoate group (Cortho-H and Cpara-H).

Figure 5:
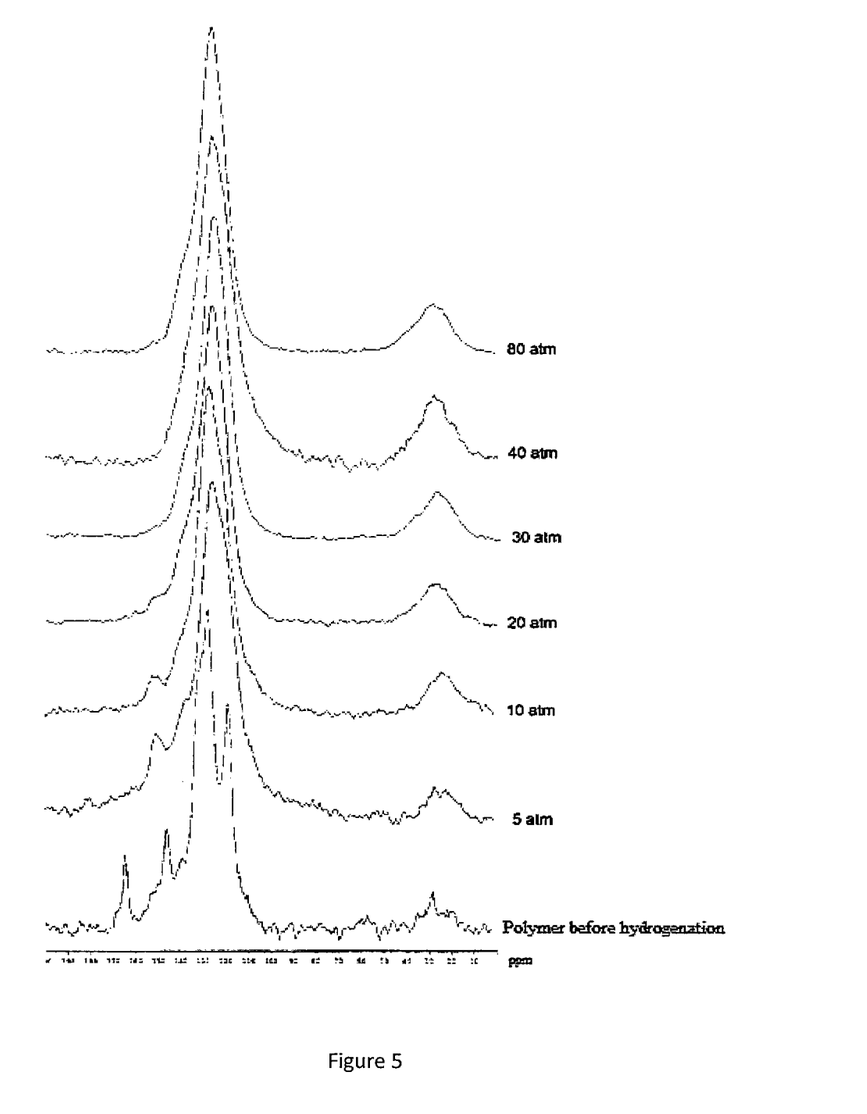
FIG. 5 shows $C^{13}$ solids nuclear magnetic resonance spectra of the hydrogenation of hydrogen donor Polymer 1 as a function of hydrogen pressure, according to an example embodiment of the present disclosure.

The C-13 nuclear magnetic resonance spectra corresponding to Polymer 1 hydrogenated at 5, 10 and 20 atm do not show the signals at 167, 147, 138 and 119 ppm. The absence of the first signal indicates the reduction of the carboxyl group (C=O) to methylene (—CH2-), whose signal must be found in the agglomeration of signals in the 100-150 ppm interval. The absence of the second (C—O-30 C(O)—C) and fourth (Cortho-H and Cpara-H) missing signals would be a consequence of the hydrogenation of one of the aromatic rings of the naphthalene unit generating the >CH—O— and >CH2 groups, whose signals must be found in the agglomeration of signals at 100-150 ppm and 15-40 ppm, respectively. The absence of the third signal at 138 ppm (C—C (O)—O) is attributed to the displacement of this signal to the agglomeration of signals at 100-150 ppm, as a consequence of the reduction of the carboxyl group. It should be pointed out that the signals of the aromatic carbons in the ortho, meta and para positions of the hydrogenated ring (Cortho, Cmeta and Cpara) must be found in the agglomeration of signals at 100-150 ppm, while the aromatic carbon attached to the oxygen atom (C—O—CH2) generates a signal at 152 ppm. In these three spectra (hydrogenation at 5, 10 and 20 atm) we can see that the signal at 152 ppm becomes smaller as the hydrogenation pressure increases and is not visible in the spectrum corresponding to hydrogenation at 30 atm, suggesting that the ether group (C—O—CH2) undergoes hydrogenolysis, generating an aromatic CH and a HO—CH2 group, with signals in the agglomeration of signals at 100-150 ppm.

Example 5

For comparison purposes, this example shows the hydrogenation of cyclohexene using a typical commercial catalyst based upon alumina-supported platinum. The procedure for these experiments was as follows: 40 milliliters of cyclohexene were fed into a 300-mL stainless steel autoclave-type reactor and 1 gram of alumina-supported platinum catalyst was placed in a mesh submerged in the cyclohexene. The reactor was closed and pressurized to 34 atm with hydrogen and then heated to 50° C. The reacting mixture was kept at this temperature under agitation for 1 hour, and then the reactor was cooled in an ice-water bath. The reaction product was analyzed by gas chromatography. The result of this experiment is shown in Table 1.

TABLE 1

| Component | Composition, wt % |
|---|---|
| Cyclohexene | 76.131 |
| Cyclohexane | 23.278 |
| Benzene | 0.592 |

Hydrogenated product yield: 23.27%.

Example 6

This example shows the effect of hydrogen donor Polymer 1 on the hydrogenation of cyclohexene. 40 milliliters of cyclohexene were fed into a 300-mL stainless steel autoclave-type reactor and 1 gram of alumina-supported platinum catalyst and 1 gram of Polymer 1 (Example 1) in a 20-mesh particle size were placed in a mesh submerged in the cyclohexene. The reactor was closed and pressurized to 34 atm with hydrogen and then heated to 50° C. The reacting mixture was kept at this temperature under agitation for 1 hour, and then the reactor was cooled in an ice-water bath. The reaction product was analyzed by gas chromatography. The result of this experiment is shown in Table 2.

TABLE 2

| Component | Composition, wt % |
|---|---|
| Cyclohexene | 33.691 |
| Cyclohexane | 65.956 |
| Benzene | 0.354 |

Hydrogenated product yield: 65.95%.

Example 7

This example shows the effect of temperature on the hydrogenation of cyclohexene using a typical commercial catalyst based upon alumina-supported platinum. The procedure described in Example 5 was followed, except for the reaction temperature, which was 100° C. instead of 50° C. The results are shown in Table 3.

TABLE 3

| Component | Composition, wt % |
|---|---|
| Cyclohexene | 15.110 |
| Cyclohexane | 70.092 |
| Benzene | 14.798 |

Hydrogenated product yield: 70.09%.

Example 8

This example shows the effect of temperature on the hydrogenation of cyclohexene using hydrogen donor Polymer 1. The procedure described in Example 6 was followed, except for the reaction temperature, which was 100° C. instead of 50° C. The results are shown in Table 4.

TABLE 4

| Component | Composition, wt % |
|---|---|
| Cyclohexene | 0.000 |
| Cyclohexane | 100.000 |
| Benzene | 0.000 |

Hydrogenated product yield: 100.00%.

Example 9

This example shows the effect of hydrogen donor Polymer 1 extruded with silica-kaolin on the hydrogenation of cyclohexene. The procedure was as follows:

40 milliliters of cyclohexene were fed into a 300-mL stainless steel autoclave-type reactor and 1 gram of alumina-supported platinum catalyst and 1 gram of Polymer 1 extruded with silica-kaolin (Example 3) in a 20-mesh particle size were placed in a mesh submerged in the cyclohexene. The reactor was closed and pressurized to 34 atm with hydrogen and then heated to 100° C. The reacting mixture was kept at this temperature under agitation for 1 hour, and then the reactor was cooled in an ice-water bath. The reaction product was analyzed by gas chromatography. The result of this experiment is shown in Table 5.

Example 10

For comparison purposes, this example shows the hydrogenation of benzene using a typical commercial catalyst based upon alumina-supported platinum. The procedure described in Example 5 was followed, except for feeding benzene to the reactor instead of cyclohexene and for the reaction temperature, which was 200° C. instead of 50° C. The results are shown in Table 6.

TABLE 6

| Component | Composition, wt % |
|---|---|
| Benzene | 86.60 |
| Cyclohexane | 13.39 |

Hydrogenated product yield: 13.39%.

Example 11

This example shows the effect of hydrogen donor Polymer 1 on the hydrogenation of benzene. The procedure described in Example 6 was followed, except for feeding benzene to the reactor instead of cyclohexene and for the reaction temperature, which was 200° C. instead of 50° C. The results are shown in Table 7.

TABLE 7

| Component | Composition, wt % |
|---|---|
| Benzene | 84.32 |
| Cyclohexane | 15.38 |

Hydrogenated product yield: 15.38%.

Example 12

This example shows the effect of hydrogen donor Polymer 1 extruded with silica-kaolin on the hydrogenation of benzene. The procedure described in Example 9 was followed, except for feeding benzene to the reactor instead of cyclohexene and for the reaction temperature, which was 200° C. instead of 100° C. The results are shown in Table 8.

TABLE 8

| Component | Composition, wt % |
|---|---|
| Benzene | 61.89 |
| Cyclohexane | 37.92 |

Hydrogenated product yield: 37.92%.

While various embodiments of the present disclosure are described with reference to various implementations and exploitations, it will be understood that these embodiments are illustrative and that the scope of the disclosure is not limited to them. Many variations, modifications, additions, and improvements are possible. Further still, any steps described herein may be carried out in any desired order, and any desired steps may be added or deleted.

Having thus described the invention, what we claim is:

1. A method for hydrogenation of organic compounds or mixtures of organic compounds, comprising:
   a. hydrogenating an organic compound or mixture of organic compounds in the presence of at least one hydrogen donor;
   wherein the hydrogen donor comprises at least one solid polymer or at least one copolymer containing a unit with two or more fused aromatic, alicyclic, or heterocyclic rings, or combinations thereof.

2. The method of claim 1, wherein the promotion of hydrogen transfer reactions takes place at temperatures between 0 and 500° C.

3. The method of claim 1, wherein said polymers or copolymers are physically and chemically stable at temperatures above the temperatures of the promoted hydrogen transfer reactions.

4. The method of claim 1, wherein a hydrogen transfer reactions takes place in the presence or absence of a reducing agent.

5. The method of claim 1, wherein a hydrogen transfer reaction takes place in the presence of hydrogen.

6. The method of claim 1, wherein said polymers or copolymers are used without any solid support material.

7. The method of claim 1, wherein said polymers or copolymers are supported on, anchored to or in physical mixture with appropriate solid materials.

8. The method of claim 1, wherein said polymers or copolymers are used alone or in combination with catalysts.

* * * * *